(12) United States Patent
Dutta et al.

(10) Patent No.: US 8,081,809 B2
(45) Date of Patent: Dec. 20, 2011

(54) METHODS AND SYSTEMS FOR OPTIMIZING HIGH RESOLUTION IMAGE RECONSTRUCTION

(75) Inventors: Sandeep Dutta, Waukesha, WI (US); Saad Ahmed Sirohey, Pewaukee, WI (US); Gopal B. Avinash, New Berlin, WI (US); John V. Skinner, New Berlin, WI (US); Patricia Le Nezet, Le Pecq (FR); DeAnn Marie Haas, Port Washington, WI (US); Sardar Mal Gautham, Waukesha, WI (US); Mukta C. Joshi, Belmont, MA (US)

(73) Assignee: General Electric Company, Schenectady, NY (US)

( * ) Notice: Subject to any disclaimer, the term of this patent is extended or adjusted under 35 U.S.C. 154(b) by 1015 days.

(21) Appl. No.: 11/562,505

(22) Filed: Nov. 22, 2006

(65) Prior Publication Data

US 2008/0118021 A1     May 22, 2008

(51) Int. Cl.
*G06K 9/00* (2006.01)
(52) U.S. Cl. ........ 382/131; 382/128; 382/276; 382/298; 382/299; 345/419; 345/420
(58) Field of Classification Search ............... 382/128, 382/131, 132, 154, 286, 254; 378/4
See application file for complete search history.

(56) References Cited

U.S. PATENT DOCUMENTS

| | | | |
|---|---|---|---|
| 5,961,457 A * | 10/1999 | Raylman et al. | 600/436 |
| 6,480,619 B1 | 11/2002 | Vuylsteke et al. | |
| 6,768,782 B1 | 7/2004 | Hsieh et al. | |
| 2002/0087069 A1 | 7/2002 | Ho et al. | |
| 2002/0106116 A1 | 8/2002 | Knoplioch et al. | |
| 2004/0252870 A1 * | 12/2004 | Reeves et al. | 382/128 |
| 2005/0043614 A1 | 2/2005 | Huizenga et al. | |
| 2005/0113960 A1 * | 5/2005 | Karau et al. | 700/182 |
| 2006/0036167 A1 | 2/2006 | Shina | |
| 2006/0061570 A1 | 3/2006 | Cheryauka et al. | |
| 2006/0079746 A1 | 4/2006 | Perret | |
| 2006/0122467 A1 | 6/2006 | Harrington | |
| 2006/0159328 A1 * | 7/2006 | Vaz et al. | 382/131 |
| 2006/0171585 A1 | 8/2006 | Rinck | |
| 2006/0239524 A1 | 10/2006 | Desh et al. | |
| 2007/0013710 A1 * | 1/2007 | Higgins et al. | 345/581 |
| 2007/0276214 A1 * | 11/2007 | Dachille et al. | 600/407 |

FOREIGN PATENT DOCUMENTS

WO    2005055008 A2    6/2005

OTHER PUBLICATIONS

Search Report, NL1034746, dated Jun. 19, 2009, pp. 9.
Heidemann, Jason E., Office Action for U.S. Appl. No. 11/562,704, Apr. 22, 2011, 37 pages, United States Patent and Trademark Office, US.

* cited by examiner

*Primary Examiner* — Sath V Perungavoor
*Assistant Examiner* — Jason Heidemann
(74) *Attorney, Agent, or Firm* — Armstrong Teasdale LLP

(57) ABSTRACT

Methods and apparatus for reconstructing a multiple resolution images of an object are provided. The method includes reconstructing a first three-dimensional image at a first resolution, determining at least one volume of interest in the generated image, and reconstructing a second three-dimensional image of the determined at least one volume of interest at a second resolution, the second resolution being higher than the first resolution such that a quantification of image structures is facilitated.

20 Claims, 4 Drawing Sheets

METHODS AND SYSTEMS FOR OPTIMIZING HIGH RESOLUTION IMAGE RECONSTRUCTION

BACKGROUND OF THE INVENTION

This invention generally relates to rotating imaging scanner systems and more particularly, to methods and systems for optimizing high resolution image reconstruction.

Detecting an accurate shape and size of small objects in CT images for example, a volume of soft plaque in a coronary vessel is affected by the resolution of the images that are being analyzed. To achieve the most accurate estimation of small volumes, the images of the object should be viewed at the highest possible resolution. However, because of limitations of storage space and workflow, acquisition of images at the highest resolution available on a CT system may not be possible.

Small airways in lungs are the early precursors of thoracic diseases for example, but not limited to chronic obstructive pulmonary disease (COPD), asthma, and bronchitis. Changes in the wall thickness and lumen of these small airways (<2 mm) facilitate indicating the progression of the disease at the very onset. Current clinical image acquisition techniques for lungs do not provide enough resolution for an accurate measurement of these airways. High-resolution reconstruction can help the accuracy but current clinical protocols do not use these because of the high number of images required to cover an entire field of view at such a reconstruction resolution. In addition, for diagnostic readings, doctors, physicians, and radiologists require images covering the full field of view of the lungs. Moreover, some of the reconstruction parameters used clinically for diagnostic reading of lung images have been found to be not suitable for quantitative analysis.

BRIEF DESCRIPTION OF THE INVENTION

In one embodiment, a method for reconstructing a multi-resolution image of an object includes reconstructing a first three-dimensional image at a first resolution, determining at least one volume of interest in the generated image, and reconstructing a second three-dimensional image of the determined at least one volume of interest at a second resolution, the second resolution being higher than the first resolution such that a quantification of image structures is facilitated.

In another embodiment, an imaging system includes a stationary member, a rotating member rotatably coupled to the stationary member wherein the rotating member includes an opened area proximate an axis about which the rotating member rotates. The imaging system also includes an x-ray source provided on the rotating member, and an x-ray detector disposed on the rotating member and configured to receive x-rays from the x-ray source. The system further includes a processor communicatively coupled to at least one of the x-ray source and the x-ray detector wherein the processor is configure to receive image data relating to an object and then reconstruct a first image at a first resolution using the received image data, determine at least one volume of interest in the generated image, and reconstruct a second image of the determined at least one volume of interest at a second resolution, the second resolution being greater than the first resolution such that a quantification of image structures is facilitated.

In yet another embodiment, a method of reconstructing a multi-resolution image of a patient includes receiving image data of at least one of a lung and a heart, reconstructing a first image at a first resolution from the received data, determining at least one volume of interest in the generated image, and reconstructing a second image of the determined at least one volume of interest at a second resolution, the second resolution being greater than the first resolution such that a quantification of image structures is facilitated.

DETAILED DESCRIPTION OF THE INVENTION

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. For example, CT imaging apparatus embodiments may be described herein as having a plurality of detector rows that are used in a certain process. Such embodiments are not restricted from having other detector rows that are not used in that process.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
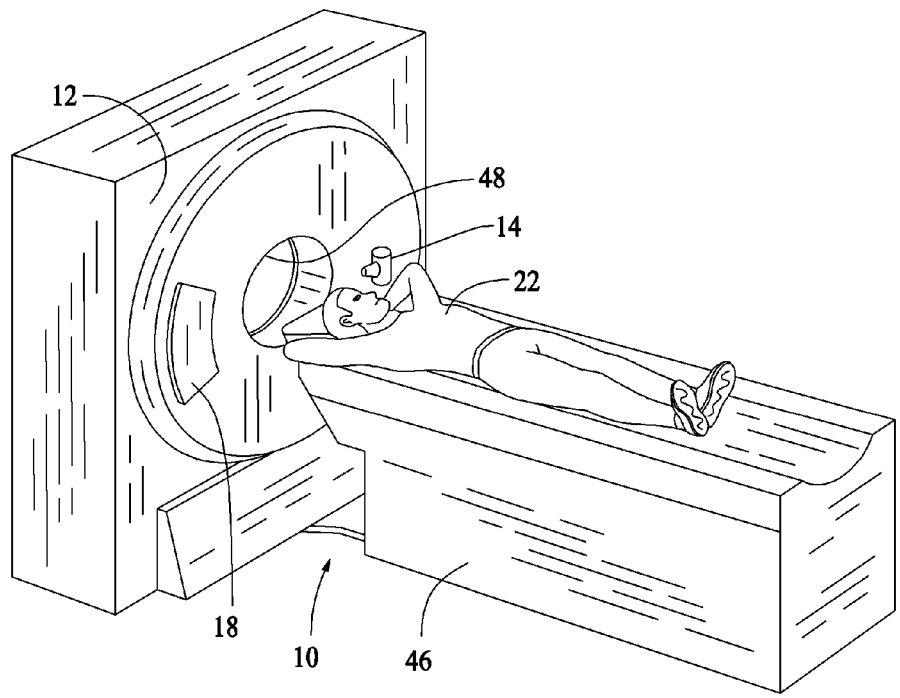
FIG. 1 is a pictorial view of a computed tomography (CT) imaging system in accordance with an embodiment of the present invention.
Figure 2:
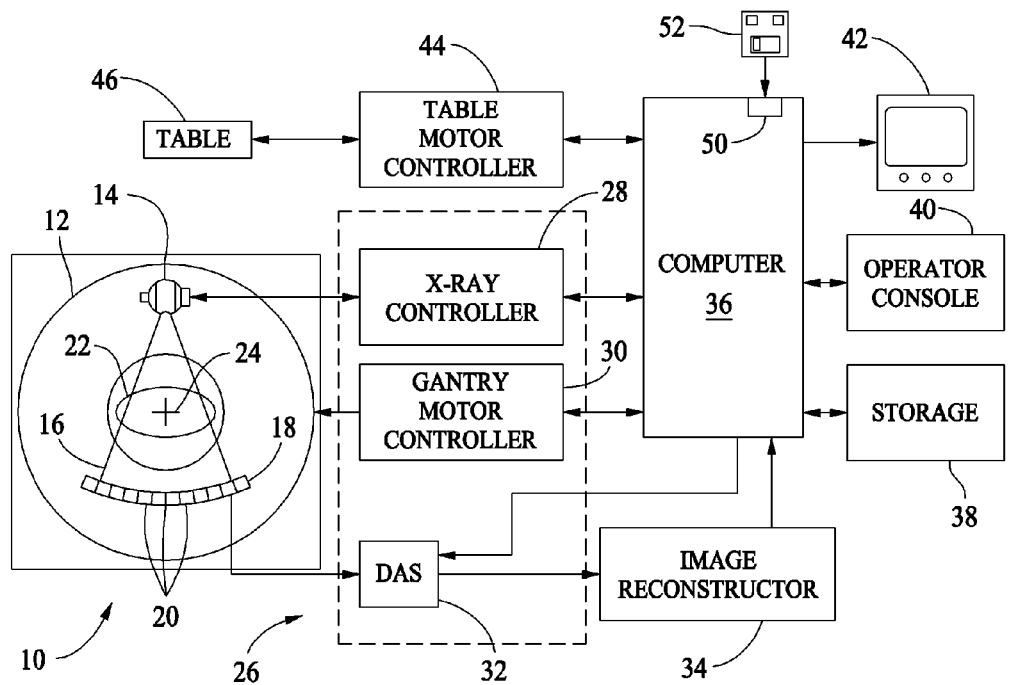
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube (CRT), liquid crystal (LCD), plasma, or another suitable display device 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

It will be understood that the block diagram of FIG. 2 is closer to a logical representation of the functions described herein than a physical block diagram. Particular hardware and/or firmware and/or software implementations of these functions can be left as a design choice to one or more people skilled in the art of logic and/or computational circuit design and/or computer programming upon such person(s) gaining an understanding of the principles of the present invention presented herein.

Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

In some configurations, detector array 18 is a multirow detector array. Radiation source 14 and multirow ray detector array 18 are mounted on opposing sides of gantry 12 so that both rotate about an axis of rotation. The axis of rotation forms the z-axis of a Cartesian coordinate system having its origin centered within x-ray beam 16. The plane defined by the "x" and "y" axes of this coordinate system thus defines a plane of rotation, specifically the plane of gantry 12.

Rotation of gantry 12 is measured by an angle from arbitrary reference position within plane of gantry 12. The angle varies between 0 and $2\pi$ radians. X-ray beam 16 diverges from the gantry plane by an angle $\theta$ and diverges along the gantry plane by angle $\phi$. Detector array 18 has a generally arcuate cross-sectional shape and its array of detector elements 20 are arranged to receive and make intensity measurements along the rays of x-ray beam 16 throughout the angles of and of radiation beam 16.

Detector array 18 comprises a 2-D array of detector elements 20 arranged in rows and columns. Each row comprises a plurality of detector elements 20 extending generally along an in-slice dimension. Each column comprises a plurality of detector elements extending generally parallel to the z-axis.

A technical effect of the present invention is the display of high resolution image areas within a relatively low resolution image. This effect is achieved in some configurations by an operator operating the CT imaging apparatus (or another apparatus on which projection data is used to generate images) using image segmentation to locate at least one volume of interest that is then reconstructed using a high resolution algorithm. The high resolution image replaces the low resolution image portion of the volume of interest for clinical study of the overall low resolution image and the high resolution volume of interest.

Figure 3:
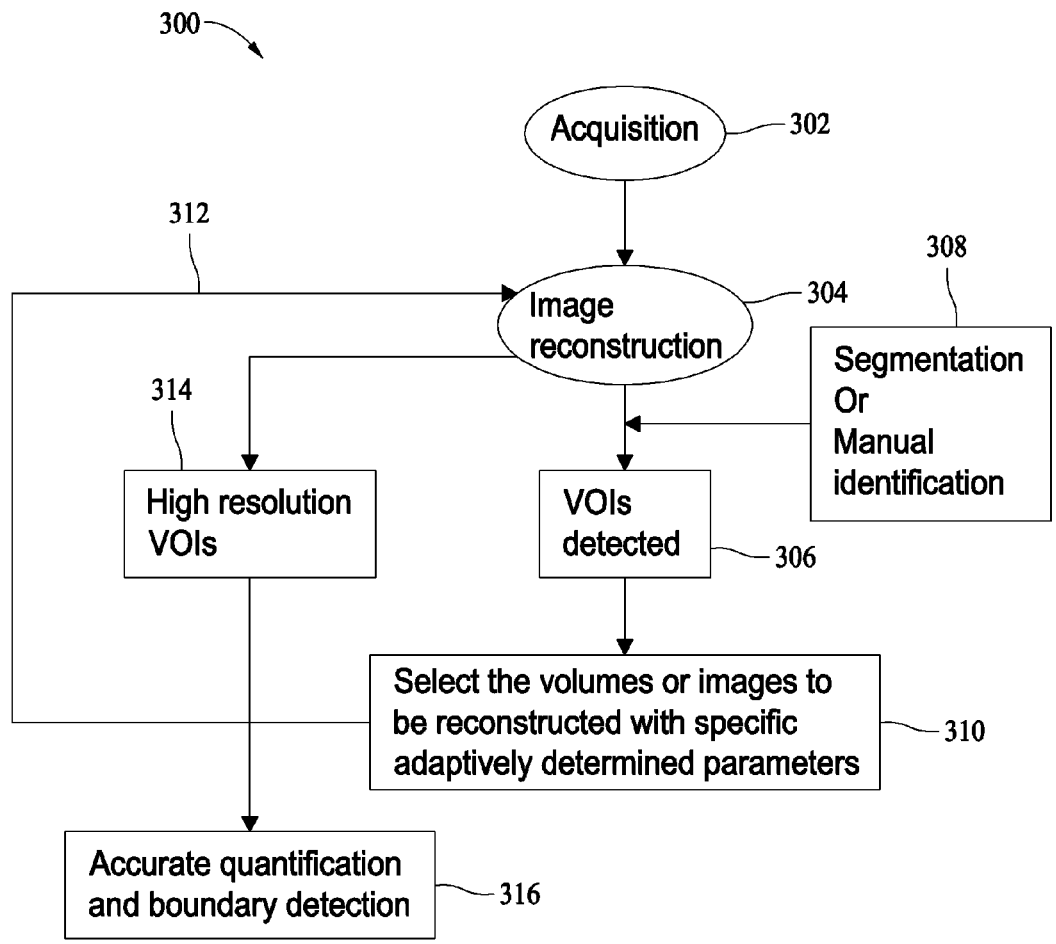
FIG. 3 is a flow chart of an exemplary method of improving segmentation, classification and quantification of small plaque deposits using an application driven optimum keyhole reconstruction technique in accordance with an embodiment of the present invention.

FIG. 3 is a flow chart of an exemplary method 300 of improving segmentation, classification and quantification of small plaque deposits using an application driven optimum keyhole reconstruction technique in accordance with an embodiment of the present invention. Method 300 includes acquiring 302 CT image data of, for example, a heart at a display field of view that covers the whole heart. Images of the heart are reconstructed 304 from the acquired data. After the original CT volume has been acquired, the reconstructed images are used to identify 306 possible volumes of interest using one or more of a plurality of processes. In the exemplary embodiment, the images are automatically segmented 308 to identify areas of potential plaque buildup. In an alternative embodiment, the volumes of interest are manually selected by a user while viewing the images. In still another embodiment, potential volumes of interest are identified and the user verifies the volumes of interest and selects the volumes of interest of greatest interest to the user. The volumes or images to be reconstructed with specific adaptively determined parameters are selected 310. The volume of reconstruction of each region can be now determined from the system. The reconstruction parameters that are optimum for each volume and study can be determined from system. The reconstruction and scan parameters are sent to 312 to a reconstruction sub-system to make only the images that correspond to each volume of interest at the desired optimum resolution for quantification. This could create new images which will contain the regions of interest selected at the highest possible resolution afforded by the scanner.

The high resolution images can be reconstructed 314 by changing the display field of view to the minimum allowable for the system configuration or by using higher resolution reconstruction kernels. Once the high resolution images are created, these new volumes are analyzed 316 for accurate segmentation and classification of the lesions and the application specific quantification of physiological parameters are generated from these high resolution volumes. Examples of some measurements include volume, location, density, composition, taper, length of each lesion. The percentage of stenosis, negative and positive remodeling of the wall of the lumen can also be quantified accurately from the new high resolution images. Similarly small airway wall thickness, diameter, lumen area, wall area can be determined accurately from the high resolution images. In another exemplary embodiment, the high resolution images are superimposed on the original resolution volume to visualize the volumes of interest in high resolution.

Figure 4:
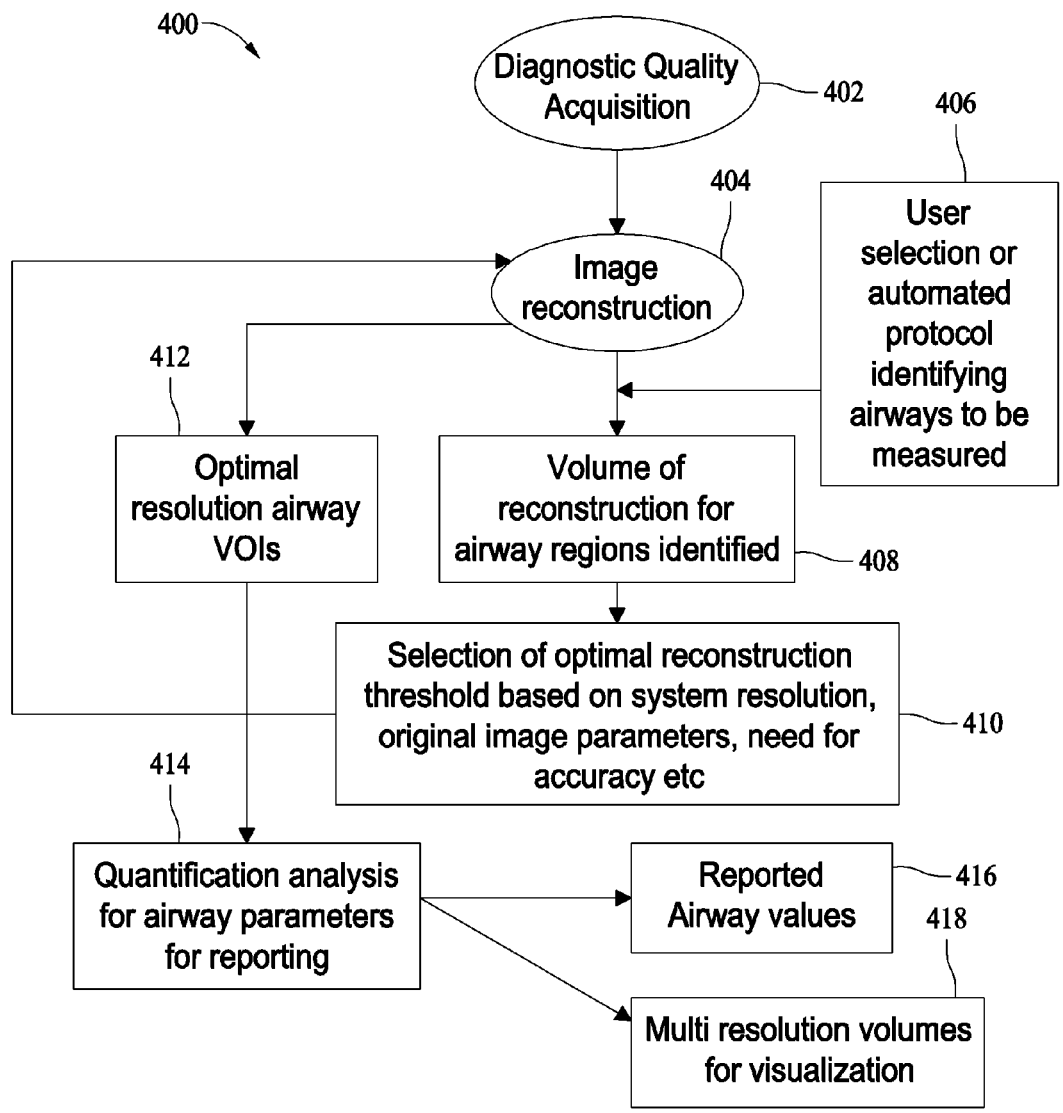
FIG. 4 is a flow chart of an exemplary method of enhancing accuracy of small airway measurements using adaptive interactive workflow-based optimum volume reconstruction in accordance with an embodiment of the present invention.

FIG. 4 is a flow chart of an exemplary method 400 of enhancing accuracy of small airway measurements using adaptive interactive workflow-based optimum volume reconstruction in accordance with an embodiment of the present invention. Method 400 includes an ability to automate the creation of optimally reconstructed images of a volume of interest for accurately measuring small airways of a patient lung. Method 400 includes acquiring 402 an initial diagnostic quality set of image data. CT images are reconstructed 404 for the lung at selected clinical reconstruction parameters and an initial airway tree segmentation is performed 406. The initial airway tree is visualized by the user in the application at any orientation. In the exemplary embodiment, after the initial segmentation, the user can use a semi-automated approach or automated approach to define clinically relevant/clinical study specific segments of interest along the airway tree. The user can then select any airway location for measurement, or an automatic measuring protocol may be invoked, for example, but not limited to measuring a halfway point on each airway segment in the airway tree. A center of reconstruction and a volume of reconstruction around the measurement location on airways in the lung are selected 408 from the information. The volume of reconstruction parameters will be optimally built based on the available system resolution, degree of resolution needed, size of the airway needed to be measured, reconstruction kernel used for the original diagnostic images. Optimal reconstruction thresholds are selected 410 based on for example, but not limited to system resolution, original image parameters, and accuracy requirements. The resultant information about the volume of reconstruction is transmitted to the reconstruction subsystem and the new images are reconstructed using the specifications laid out by the application. The small volumes of interest are reconstructed 412 at the higher optimal resolution. The new high resolution volumes of interest images are analyzed 414 and the measurements for the airways are completed and reported 416 and/or displayed 418. When the images are completed, the application will be able to load these volumes one at a time and analyze for the measurements of the airway parameters on the optimally reconstructed images.

Other exemplary embodiments of optimal reconstructions that are available include but are not limited to:

1. Performing a high-resolution reconstruction of the small volume around the airway limited by the system resolution, to get more voxels for analysis of the walls and lumen.

2. Selecting between reconstruction kernels that are optimized for quantification and diagnostic reading. For example, images reconstructed using a lung kernel may have characteristics that are not optimal for quantification but the lung kernel may perform well for diagnostic reading. Regions that are to be measured can be reconstructed using a quantification-friendly kernel and analyzed for reporting the results. Clinical studies have shown that the reconstruction kernel used for diagnostic visualization/reading may not be the most optimum and accurate one for quantitative measurements.

In one embodiment, the high-resolution volumes at each measurable location are bookmarked in the dataset when available and these images are used for visualizations of the entire lung and the high resolution images are used in a multi-resolution visualization mode. A complete set of high-resolution images for every airway that are measured would require memory space and computing power that exceed known system capabilities. Rather, the methods in accordance with various embodiments of the present invention provides higher resolution images but only at the small volume of interest around the airways or plaque lesions to be measured that have been selected automatically or manually.

Figure 5:
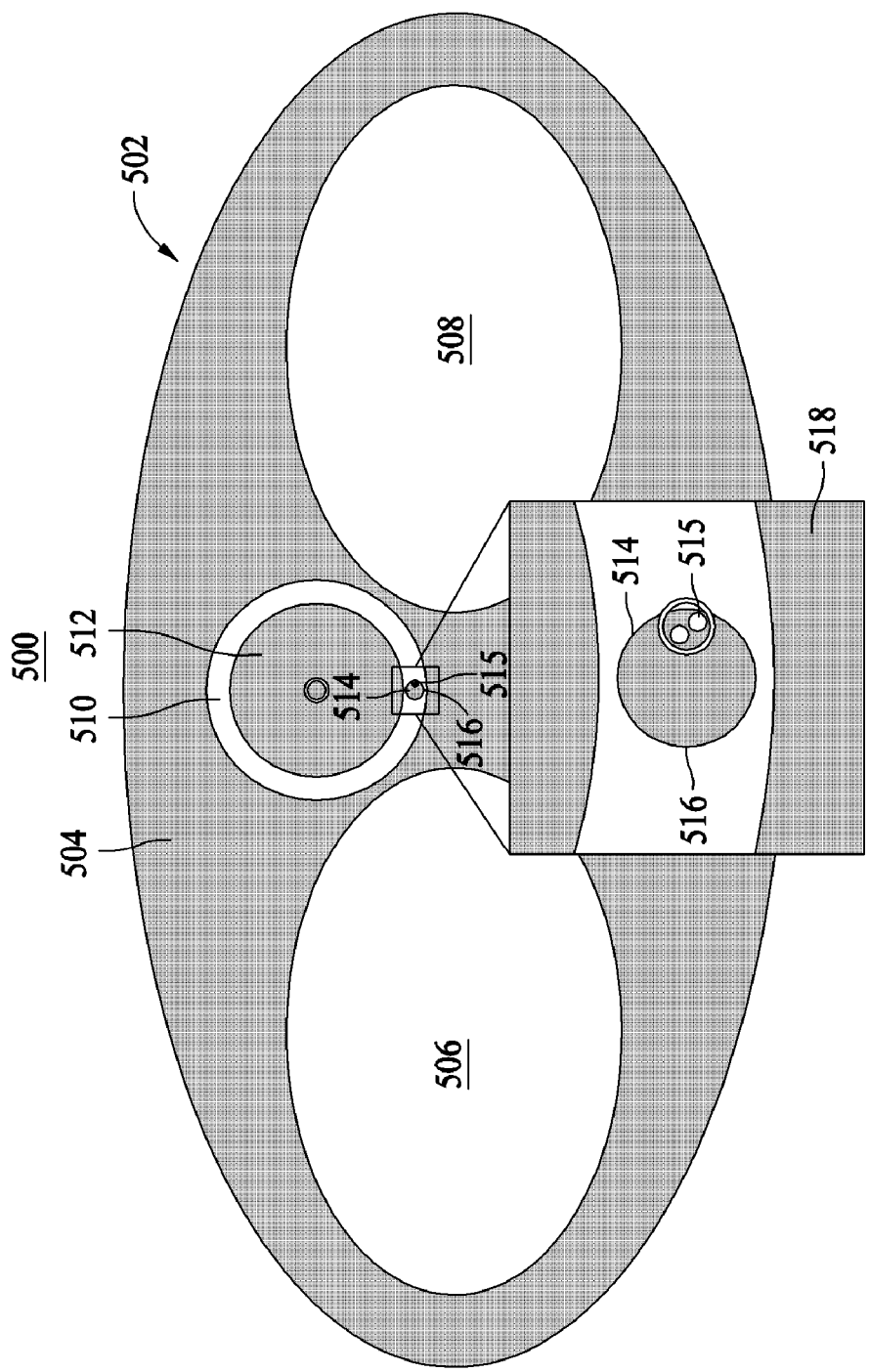
FIG. 5 is a screen shot of a multi-resolution image of a phantom generated using an embodiment of the present invention.

FIG. 5 is a screen shot 500 of a multi-resolution image of a phantom 502 generated using an embodiment of the present invention. Phantom 502 includes a structure that simulates a patient chest cavity 504 including a first lung cavity 506 and a second lung cavity 508, a heart cavity 510 and a heart structure 512. Heart cavity 510 includes a coronary vessel structure 514 that includes a generally spherical cross-section of contrast material and a plaque lesion 515 along an outer periphery 516 of vessel structure 514. Screen shot 500 also includes a high resolution enlarged area 518 of a portion of phantom 502. Area 518 shows a high resolution image of the low resolution original image of phantom 502 wherein a volume of interest was identified. The identification is done using automatic segmenting and analyzing of the low resolution image or by manual selection by a user, or a combination of both techniques. For example, an automatic segmenting and analyzing of the low resolution image using image parameters specified by a user or using predetermined standard parameters may be performed. A list of likely volumes of interest may be identified based on the image parameters and sorted according to a probability of meeting all the image parameters. The user may then select a volume of interest based on the list or a slideshow of the identified potential volumes of interest may be viewed.

Area 518 is a high resolution image of only a portion of chest cavity 504. Accordingly, the data memory and computing power requirements for generating and storing the high-resolution region image is significantly less than for generating and storing high resolution images of the entire chest cavity or portion thereof at high resolution. Maintaining the low resolution portion of the multi-resolution image also permits a user an overall view of the patient including any landmarks that may be used to facilitate clinical study of the image. Plaque lesion 515 may be analyzed using many more voxels in high resolution enlarged area 518 than is available in the low resolution portion of the image. Such high resolution facilitates identification and quantification of the various dimensions and the composition within that region associated with lesion 515.

The above-described imaging methods and systems are cost-effective and highly reliable. The various embodiments of the present invention provides, for example, an optimum high resolution reconstruction of only selected regions/volumes of interest to achieve more accurate segmentation and quantification of plaque regions, the use of selective reconstruction to obtain high resolution images of only the volumes of interest that are to be segmented, classified and measured accurately, and a mechanism to do an optimum reconstruction of only regions/volumes of interest and achieve better quantification of very small airways that are crucial for early airway disease detection The imaging methods and systems also provide an optimized iterative reconstruction driven by post processing algorithms in the image space, clinical study specific protocols to extract the imaging system resolution, an optimized workflow to leverage the available resolution in the scan file, and the imaging methods and systems provide a workflow that allows the quantification and diagnostic reading from same scan but without significantly increasing the number of images. Accordingly, the imaging methods and systems described above facilitate operation of imaging systems in a cost-effective and reliable manner.

While the invention has been described in terms of various specific embodiments, those skilled in the art will recognize that the invention can be practiced with modification within the spirit and scope of the claims.

What is claimed is:

1. A method of reconstructing a multiple resolution image of an object, said method comprising:
   reconstructing a first three-dimensional image of an airway tree at a first resolution;
   determining at least one airway measurement location on the airway tree in the first three-dimensional image comprising one of:
      manually selecting the at least one airway measurement location; and
      executing an automated measuring protocol comprising measuring a halfway point on at least one airway segment in the airway tree;
   determining a center of reconstruction and a volume of reconstruction around each measurement location to determine at least one volume of interest; and
   reconstructing a second three-dimensional image of the determined at least one volume of interest at a second resolution, the second resolution being higher than the first resolution.

2. A method in accordance with claim 1 wherein the object is a patient, said method further comprising acquiring image data of thoracic cavity including at least one lung.

3. A method in accordance with claim 2 wherein determining at least one volume of interest in the first three-dimensional image comprises determining at least one volume of interest that includes a plaque deposit.

4. A method in accordance with claim 1 further comprising displaying the first three-dimensional image and the second three-dimensional image simultaneously, wherein the second three-dimensional image is displayed within the first three-dimensional image at the location of the determined at least one volume of interest.

5. A method in accordance with claim 1 further comprising:
   segmenting and analyzing the second three-dimensional image to extract at least one feature of interest; and
   performing at least one quantification of the at least one feature of interest.

6. A method in accordance with claim 5 wherein performing at least one quantification of the at least one feature of interest comprises determining a dimension of the airway along an entire length of the airway, a dimension of the airway at a midpoint between two branch end points in the segmented airway tree, a dimension of a plaque deposit, and a composition of a plaque deposit.

7. A method in accordance with claim 1 further comprising determining reconstruction parameters for the second three-dimensional image based on at least one of reconstruction parameters for the first three-dimensional image, an imaging system solution, a determined image accuracy requirement, and an adaptively determined parameter.

8. An imaging system comprising:
   a stationary member;
   a rotating member rotatably coupled to said stationary member, said rotating member having an opened area proximate an axis about which said rotating member rotates;
   an x-ray source provided on said rotating member;
   an x-ray detector disposed on said rotating member and configured to receive x-rays from said x-ray source; and
   a processor communicatively coupled to at least one of said x-ray source and said x-ray detector, said processor configured to receive image data relating to an object and then:
      reconstruct a first image of an airway tree at a first resolution using the received image data;
      determine at least one airway measurement location on the airway tree in the first image comprising one of:
         manually selecting the at least one airway measurement location; and
         executing an automated measuring protocol comprising measuring a halfway point on at least one airway segment in the airway tree;
      determine a center of reconstruction and a volume of reconstruction around each measurement location to determine at least one volume of interest; and
      reconstruct a second image of the determined at least one volume of interest at a second resolution, the second resolution being greater than the first resolution.

9. A system in accordance with claim 8 wherein said processor is further configured to receive image data of a thoracic cavity including at least one lung.

10. A system in accordance with claim 9 wherein said processor is further configured to determine at least one volume of interest that includes a plaque deposit.

11. A system in accordance with claim 8 wherein said processor is further configured to display the second image in the first image at the location of the determined at least one volume of interest.

12. A system in accordance with claim 8 wherein said processor is further configured to:
   segment and analyze the second image to extract at least feature of interest; and
   perform at least one quantification of the at least feature of interest.

13. A system in accordance with claim 8 wherein said processor is further configured to determine a dimension of the airway along an entire length of the airway, a dimension of the airway at a midpoint between two branch end points in the segmented airway tree, a dimension of a plaque deposit, and a composition of a plaque deposit.

14. A system in accordance with claim 8 wherein said processor is further configured to determine reconstruction parameters for the second image based on at least one of reconstruction parameters for the first image, imaging system resolution, determined image accuracy requirements, and an adaptively determined parameter.

15. A method of reconstructing a multi-resolution image of a patient, said method comprising:
   receiving image data of at least one of a lung and a heart;
   reconstructing a first image of an airway tree at a first resolution from the received image data;
   determining at least one airway measurement location on the airway tree in the first image comprising one of:

manually selecting the at least one airway measurement location; and executing an automated measuring protocol comprising measuring a halfway point on at least one airway segment in the airway tree;

determining a center of reconstruction and a volume of reconstruction around each measurement location to determine at least one volume of interest; and reconstructing a second image of the determined at least one volume of interest at a second resolution, the second resolution being greater than the first resolution.

16. A method in accordance with claim 15 wherein determining at least one volume of interest comprises at least one of manually determining the at least one volume of interest and automatically determining the at least one volume of interest based on a segmentation of the received image data.

17. A method in accordance with claim 15 wherein determining at least one volume of interest comprises determining at least one volume of interest that includes a plaque deposit.

18. A method in accordance with claim 15 further comprising displaying the first image and the second image simultaneously wherein the second image is displayed within the first image at the location of the at least one determined volume of interest.

19. A method in accordance with claim 15 further comprising:

segmenting and analyzing the second image to extract at least feature of interest; and performing at least one quantification of the at least feature of interest.

20. A method in accordance with claim 15 further comprising determining a dimension of the airway along an entire length of the airway, a dimension of the airway at a midpoint between two branch end points in the segmented airway tree, a dimension of a plaque deposit, and a composition of a plaque deposit.

* * * * *

UNITED STATES PATENT AND TRADEMARK OFFICE
CERTIFICATE OF CORRECTION

| | |
|---|---|
| PATENT NO. | : 8,081,809 B2 |
| APPLICATION NO. | : 11/562505 |
| DATED | : December 20, 2011 |
| INVENTOR(S) | : Dutta et al. |

It is certified that error appears in the above-identified patent and that said Letters Patent is hereby corrected as shown below:

In Column 8, Line 45, in Claim 12, delete "at least" and insert -- at least one --, therefor.

In Column 8, Line 47, in Claim 12, delete "feature" and insert -- one feature --, therefor.

In Column 10, Lines 8-9, in Claim 19, delete "at least" and insert -- at least one --, therefor.

In Column 10, Line 10, in Claim 19, delete "feature" and insert -- one feature --, therefor.

Signed and Sealed this
Twentieth Day of March, 2012

David J. Kappos
*Director of the United States Patent and Trademark Office*